(12) United States Patent
Novotni et al.

(10) Patent No.: US 11,666,716 B2
(45) Date of Patent: Jun. 6, 2023

(54) SYSTEM FOR AUTOMATED ADJUSTMENT OF A PRESSURE SET BY A VENTILATION DEVICE

(71) Applicant: Hamilton Medical AG, Bonaduz (CH)

(72) Inventors: Dominik Novotni, Chur (CH); Thomas Laubscher, Rhaezuens (CH)

(73) Assignee: Hamilton Medical AG, Bonaduz (CH)

( * ) Notice: Subject to any disclaimer, the term of this patent is extended or adjusted under 35 U.S.C. 154(b) by 877 days.

(21) Appl. No.: 16/554,471

(22) Filed: Aug. 28, 2019

(65) Prior Publication Data

US 2020/0016349 A1 Jan. 16, 2020

Related U.S. Application Data

(63) Continuation of application No. 14/425,590, filed as application No. PCT/EP2013/066362 on Aug. 5, 2013, now Pat. No. 10,518,049.

(30) Foreign Application Priority Data

Sep. 4, 2012 (DE) ...................... 10 2012 215 662.3

(51) Int. Cl.
*A61M 16/00* (2006.01)
*A61B 5/03* (2006.01)
(Continued)

(52) U.S. Cl.
CPC .......... *A61M 16/0069* (2014.02); *A61B 5/037* (2013.01); *A61M 16/0003* (2014.02);
(Continued)

(58) Field of Classification Search
CPC .......... A61M 16/0069; A61M 16/0003; A61M 16/024; A61M 2016/0036; A61B 5/037
See application file for complete search history.

(56) References Cited

U.S. PATENT DOCUMENTS 6,435,182 B1 * 8/2002 Lutchen ................. A61B 5/085
128/200.24
8,528,553 B2 9/2013 Wysocki et al.

FOREIGN PATENT DOCUMENTS

DE 102009023963 A1 10/2010
DE 102009023965 A1 10/2010
(Continued)

OTHER PUBLICATIONS

Benditt, "Esophageal and Gastric Pressure Measurements," *Respiratory Care* 50(1):68-77, Jan. 2005.
(Continued)

*Primary Examiner* — Philip R Wiest
*Assistant Examiner* — Sarah B Lederer
(74) *Attorney, Agent, or Firm* — Seed Intellectual Property Law Group LLP (57) ABSTRACT

A system for automated adjustment of a pressure set by a ventilation device, in particular a positive and-expiratory pressure and/or a maximum airway pressure, the system comprising a pressure detection arrangement for detecting a transpulmonary pressure at the end of an expiration phase and/or for detecting a transpulmonary pressure at the end of an inspiration phase, and a device for automated adjustment of the pressure set by the ventilation device on the basis of the transpulmonary pressure detected at the end of the expiration phase and/or the transpulmonary pressure detected at the end of the inspiration phase.

20 Claims, 4 Drawing Sheets

(51) Int. Cl.
*A61M 16/20* (2006.01)
*A61B 5/085* (2006.01)
*A61B 5/08* (2006.01)

(52) U.S. Cl.
CPC .......... *A61M 16/024* (2017.08); *A61M 16/20* (2013.01); *A61B 5/08* (2013.01); *A61B 5/085* (2013.01); *A61M 2016/0027* (2013.01); *A61M 2016/0036* (2013.01); *A61M 2205/3331* (2013.01); *A61M 2205/502* (2013.01); *A61M 2210/105* (2013.01)

(56) References Cited

FOREIGN PATENT DOCUMENTS

| | | | |
|---|---|---|---|
| EP | 2091429 B1 | 8/2009 | |
| EP | 2397074 A1 * | 12/2011 | ............... A61B 5/08 |
| EP | 2397074 A1 | 12/2011 | |
| WO | 2007/082384 A1 | 7/2007 | |

OTHER PUBLICATIONS

Brochard, "What is a pressure-volume curve?" *Critical Care* 10(4), 3 pages, Aug. 10, 2006.

Grasso et al., "ECMO criteria for influenza a (H1N1)-associated ARDS: role of transpulmonary pressure", Intensive Care Medicine 38:3(2012), pp. 395-403.

Grasso et al., "ARDSnet Ventilatory Protocol and Alveolar Hyperinflation; Role of Positive End-Expiratory Pressure," *American Journal of Respiratory and Critical Care Medicine* 176:761-767, Jul. 26, 2007.

Hamilton Medical AG, "Hamilton S1—Technical Specifications," 3 pages, 2011.

Iotti et al., "Respiratory mechanics by least squares fitting in mechanically ventilated patients: applications during paralysis and during pressure support ventilation," *Intensive Care Med* 21:406-413, 1995.

Massachusetts Medical Society, "Ventilation with Lower Tidal Volumes as Compared with Traditional Tidal vols. for Acute Lung Injury and the Acute Respiratory Distress Syndrome; The Acute Respiratory Distress Syndrome Network", *The New England Journal of Medicine* 342(18): 1301-1308, May 4, 2000.

Sarge et al., "Targeting transpulmonary pressure to prevent ventilator induced lung injury", *Minerva Anestesiologica* 75(5), Minerva Medica Copyright, May 2009, pp. 293-299.

Talmor et al., "Mechanical Ventilation Guided by Esophageal Pressure in Acute Lung Injury," *The New England Journal of Medicine* 359(20):2095-2104, Nov. 13, 2008.

* cited by examiner

| FIO2 <= | 0.5 | 0.6 | 0.7 | 0.8 | 0.9 | 1.0 |
|---|---|---|---|---|---|---|
| Ptp_ee_ideal, mbar | 0 | 2 | 4 | 6 | 8 | 10 |

SYSTEM FOR AUTOMATED ADJUSTMENT OF A PRESSURE SET BY A VENTILATION DEVICE

BACKGROUND

Technical Field

The present invention relates to a system for the automated adjustment of a pressure specified or set by a ventilation device, in particular a positive end-expiratory pressure and/or a maximum airway pressure. The invention also relates to a device for machine ventilation that is provided with such a system for adjusting the set pressure, in particular the positive end-expiratory pressure and/or the maximum airway pressure.

Description of the Related Art

In today's common forms of machine ventilation, breathing gas is supplied to the patient at a positive pressure. This is why the airway pressure or the alveolar pressure during ventilation is greater than the pressure in the pleural gap surrounding the pulmonary alveoli at least during the inspiration phase. During the expiration phase, there is no pressure applied to the airway by the ventilation device, with the result that the lung tissue relaxes and the airway pressure or alveolar pressure drops. This kind of positive pressure ventilation may under certain circumstances have the effect that the pressure conditions in the respiratory tract and in the alveoli, respectively, at the end of the expiration phase become so unfavorable that there is a collapse of parts of the alveoli. The collapsed portion of the lung volume then will have to be unfolded anew in the subsequent breathing cycle. The functional residual capacity of the lungs is severely compromised, so that the oxygen saturation decreases, and also the lung tissue is permanently damaged.

In order to prevent a collapse of alveoli at the end of the expiration phase, positive-pressure machine ventilation usually is carried out using a so-called positive end-expiratory pressure, which usually is briefly referred to as PEEP. With this measure it is in many cases possible to achieve an improvement in oxygen saturation.

In ventilation with PEEP, the ventilation device permanently applies—that is, both during the inspiration phase and during the expiration phase—a predetermined positive pressure, the PEEP, to the airway. Thus, the PEEP is still applied also after the end of the expiration phase.

Ideally, the PEEP should be set large enough so that, during the expiration phase, the alveolar pressure is not, or at least only so far, below the pressure in the pleural gap that the alveolar tissue does not collapse under the effect of the pressure in the pleural gap. In other words: the PEEP is to prevent that the transpulmonary pressure—this is the pressure difference between the alveolar pressure and the pressure in the pleural gap—is less than zero or below a lower negative limit value as of which parts of the alveoli begin to collapse.

On the other hand, a too high value of the PEEP may have negative effects, especially during the inspiration phase. For, the lung tissue can be excessively stretched at very high airway pressures during the inspiration phase. Moreover, numerous studies also point out that a high value of PEEP may impede the return flow of venous blood to the heart, with corresponding negative effects on the cardiovascular system.

In clinical practice, the PEEP is set by physicians or nursing staff of intensive care units on the basis of on the basis of given physiological parameters of a patient or on the basis of known therapeutic benchmarks such as the so-called "ARDSnet Guidelines", see e.g., The Acute Respiratory Distress Syndrome Network, The New England Journal of Medicine, 2000, 342: pp. 1301-1308 or Grasso et al., American Journal of Respiratory Critical Care, 2007, 176: pp. 761-767. Such a setting usually is made in advance and is only sporadically matched or readjusted by physicians or nurses.

Actually, the PEEP should be matched to the respective prevailing transpulmonary pressure. The transpulmonary pressure in a ventilated patient, however, is not amenable to simple definition. In practice, one has to make do with estimates of the transpulmonary pressure on the basis of earlier clinical studies, such as the afforementioned ARDSnet Guidelines. Such guidelines naturally are not suited to reflect the actual state of a patient, but merely give experience values. For example, it is assumed that in patients with relatively stiff chest, a PEEP set in accordance with the ARDSnet Guidelines will often be too low, with the result that the ventilated patient is not adequately oxygenated, not even if the PEEP is adjusted in accordance with the predetermined guidelines.

A major disadvantage of known methods of deriving an optimal PEEP for a particular patient is that the necessary measurement procedures take considerable time during which patient ventilation is not possible in a regular breathing cycle. This is the situation e.g., with static pressure/volume curves (P/V curves) recorded with the aid of the "super syringe method", as described e.g., by Brochard L., Critical Care, 2006, 10: pp. 156-158.

EP 2 091 429 B1 discloses a system for automatically adjusting the PEEP, which performs a P/V maneuver at certain time intervals, in which the ventilation pressure is increased and decreased in a predetermined time pattern and the resulting change in the lung volume is detected. The PEEP is then determined based on P/V curves detected during this maneuver, on the basis of the pressure at which a volume difference between the P/V curve during inhalation and the P/V curve during exhalation becomes maximum.

Also such a P/V maneuver can be performed sporadically and under supervision only. The possibility of an automatic adjustment of the PEEP by the ventilation device is thus indeed given in principle, but cannot be utilized satisfactorily in practice.

BRIEF SUMMARY

The object underlying the one or more embodiments of the present invention consists in indicating a system that provides for the possibility of a completely or at least largely automated patient-related adjustment or readjustment of a predetermined pressure set by the ventilation device. The pressure set by the ventilation device, for example, may be the positive end-expiratory pressure PEEP. Additionally or alternatively, it should be possible to adjust or readjust the maximum airway pressure or another pressure set by the ventilation device on a completely or at least largely automated patient-related basis. In particular, the adjustment or readjustment of the pressure set by the ventilation device is to be rendered possible with as little intervention as possible in the breathing cycle or ventilation cycle (both terms will be used synonymously in the following) and possibly should necessitate no or just minor interventions by physicians or nurses.

For meeting this object, the one or more embodiments of the invention suggests a system for automated adjustment of a pressure set or specified by a ventilation device, in particular a positive end-expiratory pressure and/or a maximum airway pressure, the system comprising a pressure detection arrangement for detecting a transpulmonary pressure at the end of an expiration phase and/or for detecting a transpulmonary pressure at the end of an inspiration phase, as well as a device for automated adjustment of the pressure set by the ventilation device on the basis of the transpulmonary pressure detected at the end of the expiration phase and/or the transpulmonary pressure detected at the end of the inspiration phase. The pressure specified or set by the ventilation device is to be determined on the basis of the respective detected transpulmonary pressure, in particular such that no P/V maneuver is required to adjust the set pressure.

For example, the PEEP is to be determined based on the transpulmonary pressure detected at the end of expiration phase, in particular such that no P/V maneuver is required for adjusting the PEEP. This approach allows for setting the PEEP in an elegant way, with the transpulmonary pressure at the end of the expiration phase remaining at all times positive, at any rate never dropping significantly below zero.

In another example, additionally or alternatively to the PEEP, the maximum airway pressure can be determined on the basis of the transpulmonary pressure detected at the end of the inspiration phase. This can also be effected in such a way that there is no P/V maneuver required for setting the maximum airway pressure. For example, there can be provided a pressure detection arrangement for detecting a transpulmonary pressure at the end of an inspiration phase, and a device for automated adjustment of a maximum airway pressure set by the ventilation system, on the basis of the transpulmonary pressure detected at the end of the inspiration phase. The pressure detection arrangement may be the same as the pressure detection arrangement mentioned hereinbefore for detecting a transpulmonary pressure at the end of expiration phase. In the automated adjustment of the maximum airway pressure set by the ventilation system, it is possible furthermore to consider also the transpulmonary pressure at the end of an expiration phase as well as the set PEEP. Both values are present in relation to the particular patient and the particular situation if they are determined as part of a patient-related and situation-related determination of the PEEP on the basis of the transpulmonary pressure. The automatic determination and adjustment of the maximum airway pressure permits to exclude damage to the lung tissue due to excessive airway pressure during the inspiration phase. Here too, it may be considered that different upper limits for the airway pressure may be applicable for different patients.

For determining the transpulmonary pressure, the pressure detection arrangement may comprise a sensor device designed for determining an alveolar pressure on the one hand, and a sensor device designed for determining an esophageal pressure on the other hand. The respective transpulmonary pressure can then be determined under certain circumstances from a difference between the respective alveolar pressure and the respective esophageal pressure. The term respective is to mean that the determination of the alveolar and esophageal pressures, respectively, is to take place at the end of an expiration phase and/or at the end of an inspiration phase. It has been investigated in various studies to what extent an esophageal pressure detected by means of a probe inserted in the esophagus corresponds sufficiently well to the pressure in the pleural gap which is difficult to detect, in order to permit use thereof for approximately determining the transpulmonary pressure, see e.g., Talmor D. et al., New England Journal of Medicine, 2008, 359: pp. 2095-2104. The integration of such an esophageal pressure measurement in an automated system for machine ventilation, as suggested according to a development of one embodiment of the present invention, leads to the possibility of ventilating patients with a PEEP that is individually matched to the same and their course of disease, and/or with maximum airway pressure. The PEEP and/or the maximum airway pressure therefore can always be set relatively high, with the associated benefits in terms of oxygenation and effective use of the entire lung tissue. However, it is never so high that impairments arise with regard to excess stretching of the lung tissue or in the cardiovascular system. It has been found that the suggested esophageal pressure measurement is sufficiently good to handle under clinical conditions. Above all, there can also be rendered possible a sufficiently accurate and reproducible measurement of the esophageal pressure in many cases, especially when patients, during artificial ventilation remain lying in a substantially defined position. In addition, it has been found that the esophageal pressure measured under such conditions sufficiently well reflects the actual value of the pressure in the pleural gap to achieve an automated adjustment of the PEEP and/or the maximum airway pressure on a largely optimum level.

The sensor device for the determination of the esophageal pressure may comprise e.g., a catheter with balloon probe that can be introduced into the esophagus for detection of the esophageal pressure. Such catheters are known e.g., from Benditt J., Resp. Care, 2005, 50: pp. 68-77.

The determination of the alveolar pressure can be effected in accordance with a determination of the airway resistance, as well as measurements of the gas flow in the airway at the end of the expiration phase and/or at the end of the inspiration phase. From these data, which are good to detect by means of a suitable sensor device, the respective alveolar pressure can be determined in quite good approximation if one also knows the pressure at the entrance or inlet of the airway. Measurements of the gas flow are often already provided anyway in a ventilation device and can be carried out virtually in real time. The determination of the airway resistance can be effected e.g., by means of statistical regression methods, such as described in Lotti I. A. et al., Intensive Care Med., 1995, 21: 406-413. For determining the pressure at the inlet of the airway, there may be provided an airway sensor arranged at the tube beginning. As an alternative, such a pressure sensor could also be associated with an airway inlet valve of the ventilation device, so that the tube proper, which as a rule is used only once, would not have to be provided with a pressure sensor of its own. The alveolar pressure at the end of the expiration phase or at the end of the inspiration phase is then obtained in approximated form by a difference between the respective pressure at the airway inlet and the product of airway resistance and gas flow at the end of the expiration phase/gas flow at the end of the inspiration phase.

The type of determination of the alveolar pressure described hereinbefore can be realized quasi in real time and without interrupting the breathing cycle or ventilation cycle. However, it has the disadvantage of limited accuracy. A more accurate determination of the alveolar pressure is permitted by a sensor device comprising an arrangement for producing a short-time occlusion of the airway and configured such that it determines the alveolar pressure at the end of an expiration phase and/or the alveolar pressure at the end of an inspiration phase by way of the pressure at the airway entrance determined during an occlusion performed at the end of the expiration phase and/or at the end of the inspiration phase. This kind of determination of the alveolar pressure is relatively accurate. However, it has the disadvantage that the breathing cycle or ventilation cycle briefly has to be interrupted during occlusion. The occlusion should be chosen so long that a pressure balance between the pressure in the alveoli and the pressure at the airway inlet can be effected, i.e., such that a moment is reached in which the gas flow is stopped. Typically, such an occlusion lasts 2 to 4 s. Such an occlusion maneuver can be provided in regular intervals, such as every two minutes or approx. every 20 breaths.

A brief occlusion of the type described can be brought about in simple manner, when both an airway inlet valve and an airway outlet valve of the ventilation device are closed for a predetermined occlusion period. Both valves are present anyway and only need to be controlled in correspondingly synchronous manner.

The two types of determination of the alveolar pressure described hereinbefore can be particularly well combined. For example, it is possible to proceed such that at the end of each inspiration phase and at the end of each expiration phase (or also at the end of every second, third, fourth, etc. expiration phase/inspiration phase), the alveolar pressure is determined on the basis of the respective prevailing gas flow, the airway resistance and the respective prevailing pressure at the airway entrance. If, on the basis of the thus determined alveolar pressure, or the PEEP or maximum pressure resulting therefrom, the necessity arises during the inspiration phase to set a new PEEP and/or to set a new maximum airway pressure, it is possible in the subsequent breathing cycle or ventilation cycle to determine the alveolar pressure on the basis of an occlusion effected at the end of the expiration phase or at the end of the inspiration phase, and the new PEEP and/or the new maximum airway pressure can then be determined taking into account the more precise results of this determination.

Thus, it can be monitored breath for breath whether the set PEEP and/or the set maximum airway pressure should be altered due to changes in physiological parameters, in particular the transpulmonary pressure, of a particular patient. There are only minimum interventions in the breathing cycle or ventilation cycle of the patient necessary, as a brief occlusion at the end of the expiration phase or at the end of the inspiration phase is necessary only when a change in the PEEP and/or the maximum airway pressure is actually indicated. As long as the set PEEP and/or the set maximum airway pressure is monitored without changes being indicated, no interventions whatsoever need to be made in the breathing cycle or ventilation cycle.

Using the proposed system, it is readily conceivable that in a respective breathing cycle or ventilation cycle the PEEP and/or the maximum airway pressure is determined for the subsequent breathing cycle, i.e., that the PEEP and/or the maximum airway pressure is breath-monitored, and if necessary readjusted. The readjustment of the PEEP and/or the maximum airway pressure can take place in upward or downward direction. The readjustment of the PEEP and/or the maximum airway pressure is not carried out on the basis of predetermined benchmarks, but on the basis of physiological parameters, which are individually and currently determined for the patient, especially on the basis of the transpulmonary pressure determined individually and currently for the patient.

In order to avoid too frequent changes in PEEP and/or maximum airway pressure, the PEEP and/or the maximum airway pressure may not only be determined on the basis of the current breathing cycle, but it is also possible to make use of the values of the PEEP and/or the maximum airway pressure determined in several preceding breathing cycles. It is thus possible to compensate for measurement inaccuracies or static fluctuations, so that the PEEP and/or the maximum airway pressure is not readjusted before the physiological condition of the patient shows an actual trend. A similar effect can be achieved by an additional or alternative comparison of the PEEP and/or maximum airway pressure determined for the subsequent breathing cycle with the PEEP and/or maximum airway pressure set for the current breathing cycle, with the proviso that the PEEP and/or the maximum airway pressure is changed only if the difference between the two values exceeds a predetermined threshold value.

For example, it is possible to proceed such that, at the end of each breathing cycle, a preliminary value for the PEEP and/or the maximum airway pressure is determined in the subsequent breathing cycle by way of the gas flow in the airway at the end of the expiration phase and/or at the end of the inspiration phase and by way of the airway resistance. Only if the preliminary value for the PEEP and/or the maximum airway pressure in the subsequent breathing cycle differs from the set value for the PEEP and/or the maximum airway pressure by a predetermined threshold value or more, will a brief occlusion be performed in the subsequent breathing cycle, and a new value for the PEEP and/or the maximum airway pressure will be determined.

The suggested system can definitely make use of predetermined guidelines, as defined e.g., in the ARDSnet Guidelines described above. One possibility consists in using such guidelines as basis, with the value of the PEEP in a subsequent breathing cycle being determined in accordance with a deviation of the transpulmonary pressure at the end of an expiration phase, as determined in one or several preceding breathing cycles, from a normalized transpulmonary pressure at the end of an expiration phase.

For example, the determination of the value for the PEEP in the subsequent breathing cycle can take place in accordance with the following formula:

$$PEEP\_n+1 = PEEP\_n + f^*(Ptp\_ee\_\text{norm} - Ptp\_ee\_n)$$

with:
PEEP_n+1: PEEP in the subsequent breathing cycle
PEEP_n: PEEP in the current breathing cycle or
    PEEP in m preceding breathing cycles
Ptp_ee_norm: normalized transpulmonary pressure
    at the end of the expiration phase,
Ptp_ee_n: transpulmonary pressure at the end of the expiration phase
    as determined in the current breathing cycle
    or in m preceding breathing cycles,
    with m≥1,
$0 \leq f \leq 1$, in particular $0.01 \leq f \leq 0.8$, in particular $0.05 \leq f \leq 0.5$, in particular f=0.2.

The normalized transpulmonary pressure at the end of the expiration phase can be determined, for example, by way of a predetermined relationship between the normalized transpulmonary pressure at the end of the expiration phase and the oxygen fraction of the breathing gas. Such relationships are defined, for example, in the above-mentioned ARDSnet Guidelines in the form of corresponding tables.

A starting value for the PEEP can be determined e.g., by way of a predetermined relationship between the PEEP and the oxygen fraction of the breathing gas FiO2. In the past, it has turned out that such a predetermined relationship is often dependent on whether the oxygen fraction of the breathing gas FiO2 is increased or decreased in comparison with the oxygen fraction set before, so that it is advisable to consider this trend of a changed oxygen fraction of the breathing gas in the selection of the appropriate relationship.

For determining the maximum airway pressure in the subsequent breathing cycle, it is advantageous to determine a difference between the airway pressure at the end of an inspiration phase, as detected in one or more preceding breathing cycles, and the PEEP applied in one or more preceding cycles.

The maximum airway pressure in the subsequent breathing cycle can then be determined using the following formula:

$$Paw\_max\_n+1 = [(Paw\_ei\_n - PEEP\_n)/(Ptp\_ei\_n - Ptp\_ee\_n)] * Ptp\_ei\_max$$

with:
Paw_max_n+1: maximum airway pressure
 in the subsequent breathing cycle;
Ptp_ei_max: predetermined maximum transpulmonary pressure at the end
 of the inspiration phase;
Ptp_ei_n: transpulmonary pressure at the end of the inspiration phase
 determined in the current breathing cycle
 or in m preceding breathing cycles,
Ptp_ee_n: transpulmonary pressure at the end of the expiration phase
 determined in the current breathing cycle
 or in m preceding breathing cycles;
Paw_ei: airway pressure at the end of the inspiration phase
 determined in the current breathing cycle
 or in m preceding breathing cycles;
PEEP_n: peep determined in the current breathing cycle
 or in m preceding breathing cycles
 with m≥1.

The maximum transpulmonary pressure at the end of the inspiration phase is to be determined e.g., on the basis of predetermined standard values. Such standard values can be between 15 and 20 cm $H_2O$.

A suitable starting value for the maximum airway pressure at the end of the inspiration phase can also be identified on the basis of predetermined standard values. A maximum airway pressure at the end of the inspiration phase of 30 cm $H_2O$ has been found as well suitable.

One or more embodiments of the invention further relates to a device for machine ventilation of patients, comprising a system for automated adjustment of a pressure set by the ventilation device, in particular a positive end-expiratory pressure and/or a maximum airway pressure, as described hereinbefore. The ventilation device operates in particular in accordance with the positive pressure principle, with the possibility of performing the ventilation in pressure-controlled or volume-controlled manner, with mixed forms being possible as well. The ventilation device in principle may comprise all ventilation forms known; in addition to ventilation modes with total takeover of the ventilation through the machine, there are also conceivable ventilation modes in which the ventilation device supports the spontaneous breathing of the patient by intermittent machine ventilation sequences and/or individual spontaneous breaths of the patient.

A further, independent aspect of the present invention relates to a method for automated adjustment of a pressure set by a ventilation device, in particular a positive end-expiratory pressure (PEEP) and/or a maximum airway pressure, in which method a transpulmonary pressure at the end of an expiration phase and/or a transpulmonary pressure at the end of an inspiration phase is detected and the pressure set by the ventilation device is adjusted on the basis of the transpulmonary pressure detected. Such a method can be developed further by one or more of the features described before with reference to the system for automated adjustment of a pressure set by a ventilation device.

BRIEF DESCRIPTION OF THE SEVERAL VIEWS OF THE DRAWINGS

The invention will be explained in detail in the following by way of embodiments shown in the drawings in which.

DETAILED DESCRIPTION

Figure 1:
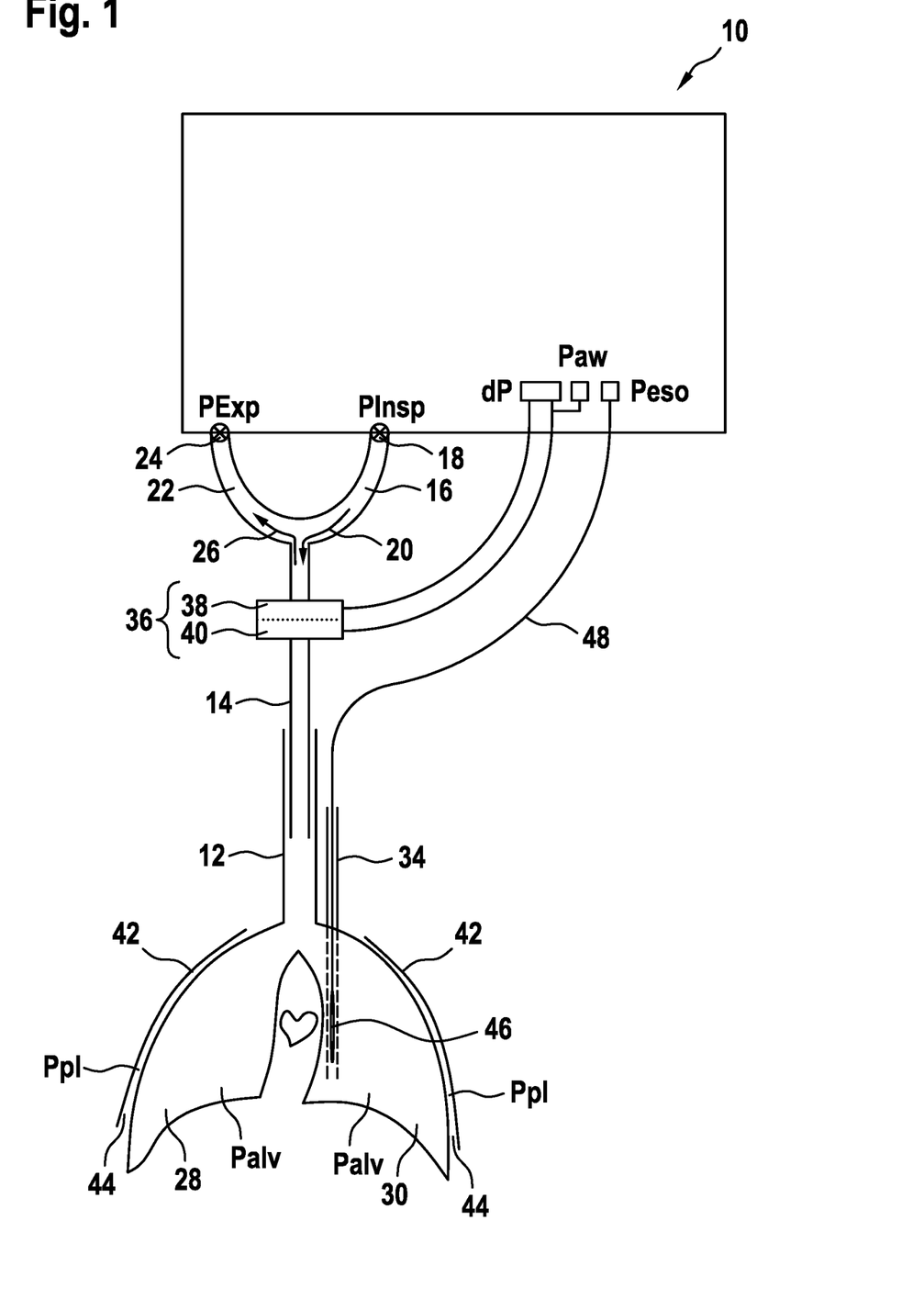
FIG. 1 shows a highly schematic illustration of the essential elements of a ventilation device including intubated trachea and thorax of a ventilated patient.

FIG. 1 shows the essential elements of a ventilation device 10 in a highly schematic representation and in the form of a block diagram. The ventilation device 10 is shown in FIG. 1 in a state with intubated windpipe (trachea) 12 of a ventilated patient. In addition to the trachea 12, FIG. 1 very schematically illustrates the lung lobes 28, 30, the heart 32, the gullet (esophagus) 34 and the chest wall 42 of the patient. The tube 14 of the ventilation device 10 is pushed a certain distance into the trachea 12, usually via the mouth opening (not shown) of the patient, in order to supply breathing gas to the airway. Exhaled air is discharged via the tube 14 as well, which branches at its upstream end into a first end 16 and a second end 22. The first end 16 is connected via an airway inlet valve 18 to an airway inlet connector of the ventilation device 10 for applying an inspiration pressure PInsp. In the open position of the airway inlet valve 18, the inspiration pressure PInsp is applied to the airway. The second end 22 is connected via an airway outlet valve 24 to an airway outlet connector of the ventilation device 10 for application of an expiration pressure PExp. In the open position of the airway outlet valve 24, the expiration pressure PExp is applied to the airway.

Both the inspiration pressure PInsp and the expiration pressure PExp are generated by the ventilation device 10 according to predetermined time patterns, such that breathing gas to be inhaled during an inspiration phase flows towards the lungs 28, 30 of the patient, as shown in FIG. 1 by arrow 20, and the breathing gas to be exhaled during an expiration phase flows back from the lungs 28, 30 of the patient, as indicated by arrow 26. During the inspiration phase, the airway inlet valve 18 normally remains open, and inspiration pressure PInsp—which as a rule is larger than the expiration pressure PExp—is applied to the airway entrance.

During the expiration phase, the airway inlet valve 18 is closed and the airway outlet valve 24 is open. In this situation, the expiration pressure PExp is applied to the airway.

In connection with the present invention, any forms of known ventilation patterns can be used, for example, pressure-controlled ventilation modes, volume-controlled ventilation modes or also ventilation modes combining pressure-controlled and volume-controlled aspects. In addition to purely machine-controlled ventilation modes, in which the time course of the inspiration pressure PInsp and possibly also the expiration pressure PExp are determined by the ventilation device 10, there are also ventilation modes conceivable in which spontaneous breathing efforts of the patient can either support the machine ventilation, or the machine ventilation serves to support spontaneous breathing endeavors of the patient. With such types of ventilation, the time course of inspiration pressure PInsp and expiration pressure PExp, respectively, and often also the position of the inlet valve 18 and outlet valve 24, respectively, are not determined solely by the ventilation device 10 but are influenced also by the spontaneous breathing endeavors of the patient.

The breathing gas may contain ambient air, but will usually contain a predetermined proportion of pure oxygen, hereinafter referred to as FiO2, which is higher than the oxygen content of the ambient air. Moreover, the breathing gas as a rule is also humidified.

The flow of breathing gas at the airway entrance is determined by means of an airway entrance flow sensor 36. The airway entrance flow sensor 36 is based on detecting a pressure difference dP between an input volume 38 and an output volume 40 communicating with the input volume 38, and provides for a determination of the breathing gas mass flow at the airway entrance. It is quite easily possible to derive from the pressure signal in the output volume 14 at the same time the value of the airway inlet pressure Paw.

The pressure prevailing in the alveoli of the lungs 28, 30 is indicated in FIG. 1 by Palv. This pressure is dependent on the airway inlet pressure Paw and the flow of breathing gas V into the lungs and out of the lungs, respectively, as well as the airway resistance R. In the event of a pressure balance between airway entrance and alveoli, the alveolar pressure Palv is equal to the airway inlet pressure. The consequence of such a pressure balance is that the flow of breathing gas V comes to a standstill. For example, a brief occlusion maneuver of the airway, i.e., airway inlet valve 18 and airway outlet valve 24 remain simultaneously closed, can result in a pressure balance. In this regard, the occlusion manoeuver needs to be just as long that the gas flow V in the airway comes to a stop. Generally, this takes between 1 and 5 s. In this state, the alveolar pressure Palv can be determined by determining the airway inlet pressure Paw.

Both in case of physiological respiration as well as in case of machine ventilation, the flow of breathing gas is determined by a pressure difference between the alveolar pressure Palv and airway inlet pressure Paw.

In case of purely physiological breathing, a negative pressure differential, i.e., a vacuum, between the alveolar pressure Palv and airway entrance pressure Paw is generated for inhaling, by expansion of the thorax (indicated at 42 in FIG. 1) and associated lowering of the pressure Ppl in the pleural gap 44 formed between the thorax 22 and the lungs 28, 30. Exhalation takes place passively by relaxation of the thorax and elastic recovery of the lung tissue. For this reason, the pressure in the pleural gap Ppl in case of physiological respiration is always lower than the alveolar pressure Palv. The transpulmonary pressure Ptp defined as difference between the alveolar pressure Palv and the pressure in the pleural gap Ppl is thus generally positive and becomes zero in case of a complete pressure balance.

With machine ventilation, the breathing gas is pumped into the lungs with positive pressure. For this reason, the airway inlet pressure Paw=PInsp in case of machine ventilation, during the inspiration phase, is greater than the alveolar pressure Palv, and the latter in turn is greater than the pressure in the pleural gap Ppl. It follows from these pressure conditions that the transpulmonary pressure Ppl in case of machine ventilation is positive during inspiration. During expiration, an airway pressure PExp is applied to the airway entrance which is lower than the alveolar pressure Palv so that breathing gas flows out from the alveoli. In case of a very small airway pressure PExp, it may happen that at the end of expiration, when only very little gas is still present in the lungs, the pressure in the pleural gap Ppl exceeds the alveolar pressure Palv to such an extent that a portion of the alveoli of the lungs collapses. The transpulmonary pressure Ptp is negative then.

The collapse of the alveoli can be prevented when an additional positive pressure is applied to the airway entrance in the expiration phase as well. A positive airway pressure then is permanently, i.e., both during the inspiration phase and during the expiration phase, to the airway entrance. This positive airway pressure is referred to as positive end-expiratory pressure or PEEP.

The transpulmonary pressure Ptp is therefore a suitable parameter for setting or adjusting the PEEP. However, the transpulmonary pressure Ptp cannot be ascertained by direct detection, and cannot be determined, either, from the pressures that are detected regularly during machine ventilation, as described hereinbefore.

FIG. 1 schematically shows an additional an additional pressure probe 46 for measuring the pressure in the esophagus (trachea) 34, referred to as esophageal pressure Peso. The probe 46 in the form of a so-called balloon probe is attached to a catheter 48 introduced into the esophagus 34. The balloon probe 46 abuts on the inside of the wall of the esophagus 34, and delivers the pressure acting in the esophagus at the site of balloon probe 46. With proper positioning of the patient, this pressure corresponds in good approximation to the pressure Ppl in the pleural gap. The balloon probe 46 described for detecting the esophageal pressure Peso and the handling of this probe are described in Benditt J., Resp. Care, 2005, 50: pp 68-77.

If it is desired to determine the transpulmonary pressure Ptp, information on the alveolar pressure Palv is necessary in addition to the pressure in the pleural gap Ppl. A rather elegant possibility for determining the alveolar pressure at a specific time t is offered by the detection of the breathing gas flow V(t), which can be performed using the flow sensor 36. It is then possible to conclude the alveolar pressure at the time t in accordance with the relationship: $Palv(t)=Paw(t)-R*V(t)$, where R denotes the airway resistance. The airway resistance for one and the same patient is a variable which in essence does not vary or varies only relatively slowly, and can be determined by methods known in the art. For example, reference is made to Iotti I. A. et al., Intensive Care Med, 1995, 21: 406-413. Due to the fact that, for determining a suitable PEEP, above all the transpulmonary pressure at the end of the expiration phase Ptp_ee is of relevance, a determination of the alveolar pressure Palv in connection with an automated adjustment of the PEEP will be made preferably at the end of the expiration phase, according to the formula:

$$Ptp\_ee = Palv\_ee - Peso\_ee = Paw\_ee - R*V\_ee - Peso\_ee.$$

The PEEP should then be set such that Ptp_ee remains always positive, at any rate never drops markedly below zero.

Unfortunately, the described method of determining the alveolar pressure Palv, which is quite easy to implement in an automated ventilation device 10, permits only a comparatively rough estimate of the appropriate PEEP. This is mainly due to the relatively inaccurately assessable airway resistance R, which moreover as a rule will be subject to a certain trend in the course of a therapy.

Figure 2:
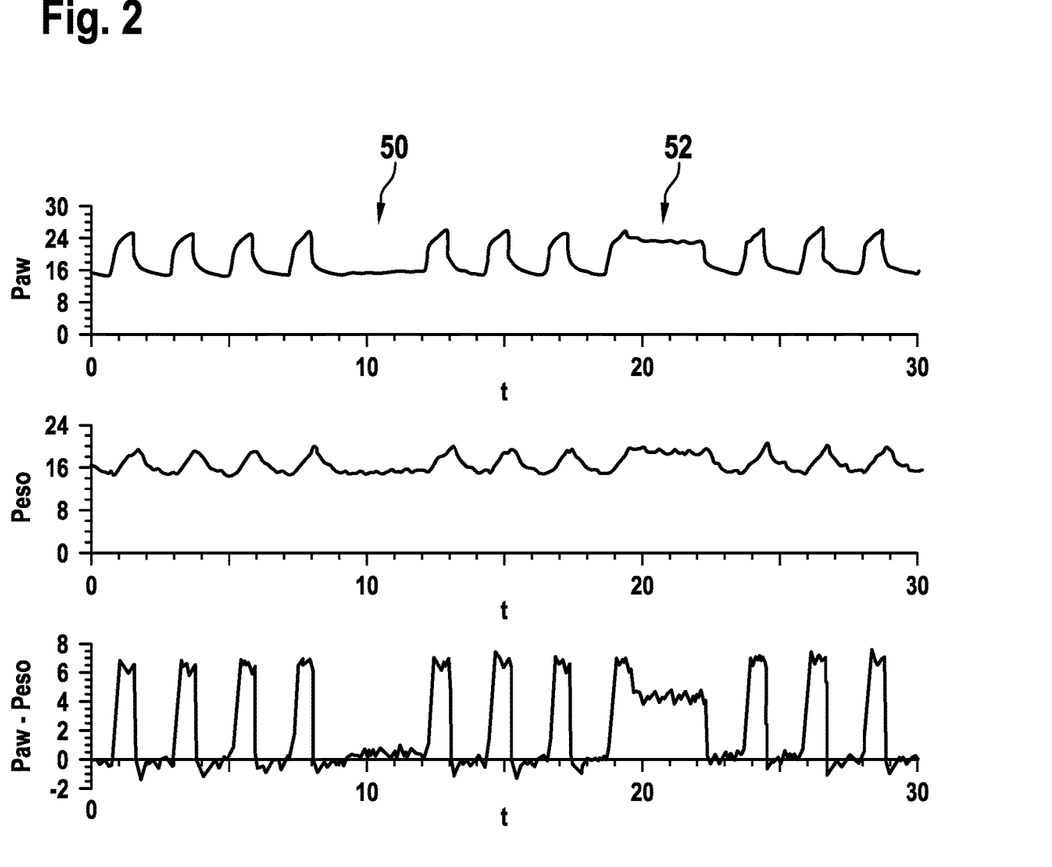
FIG. 2 shows time charts of the airway inlet pressure Paw (above), esophageal pressure Peso (middle) and the difference Paw−Peso of both pressures during several successive breathing cycles with machine ventilation including occlusion maneuvers.

An alternative method of determining the alveolar pressure Palv is based on a short-time occlusion maneuver, in which both the airway inlet valve 18 and the airway outlet valve 24 remain closed at the same time. In this occlusion state, there is created an equilibrium of the pressures prevailing in the airway. If such an occlusion maneuver is performed at the end of an expiration phase, the pressure arising after a sufficiently long occlusion in the airway will be in good approximation equal to the alveolar pressure Palv at the end of the expiration phase. This pressure can be detected quite easily by means of the pressure probe for measuring the airway pressure Paw, which is arranged at the airway entrance. In FIG. 2, this situation is shown at the location bearing numeral 50.

FIG. 2 illustrates, one above the other, time charts of the airway pressure Paw (above), the esophageal pressure Peso measured with the balloon probe 46 (middle) and the difference Paw–Peso of both pressures during several successive breathing cycles between which occlusion maneuvers were carried out as well. One can clearly see the individual breathing cycles, each including an inspiration phase (high increasing airway pressure Paw) and an expiration phase (decreasing airway pressure Paw). The esophageal pressure Peso follows the airway pressure Paw, however in attenuated form. The pressure differential Paw–Peso illustrated in the lower curve would quite well correspond to the transpulmonary pressure Ptp—with a sufficiently slow flow of breathing gas so that there is always effected a pressure balance. However, this prerequisite does not exist in practical application because of the greatly changing breathing gas flow, apart from the locations referenced 50 and 52 at which a brief occlusion was carried out at the end of an expiration phase (50, between about 8 s and 12 s) and a brief occlusion was carried out at the end of the inspiration phase (52, between about 18.5 s and 24.5 s). The occlusion lasted in both cases about 4 s. In the example chosen, this corresponds approximately to the duration of one breathing cycle. In general, the occlusion should take so long that a pressure balance takes place in the airway and the gas flow in the airway thus comes to a standstill.

At the end of the location in the time chart (approx. between 11 s and 12 s, for example, in the last approx. 200 ms of occlusion), the pressure Paw–Peso illustrated in the third line in FIG. 2 corresponds in quite good approximation to the transpulmonary pressure at the end of the expiration phase Ptp_ee. For the determination of Ptp_ee, it would be possible e.g., to form the average value of Paw–Peso over the period of time mentioned. At the end of the location designated 52 in the time chart (approx. between 21.5 s and 22.5 s, for example, in the last approx. 200 ms of occlusion), the pressure Paw–Peso illustrated in the third line corresponds in quite good approximation to the transpulmonary pressure at the end of the inspiration phase Ptp_ei. For the determination of Ptp_ei, it would be possible, for example, to form the average value of Paw–Peso over the period of time mentioned.

The determination of the transpulmonary pressure Ptp using the occlusion maneuver described is more accurate than the method described above using the airway resistance R. However, it requires performing an occlusion maneuver at the end of an expiration phase or at the end of an inspiration phase. Therefore, this method naturally interferes with the breathing cycle, and this all the more the longer the duration of occlusion as compared to the duration of the breathing cycle. For this reason, it is advisable to check quite often, for example after each breath or every n breaths (n>1), by means of the airway resistance method whether a set value of the PEEP and/or a set value of the maximum airway pressure is still within the scope of the requirements or whether a resulting value of the transpulmonary pressure Ptp_ee is still within certain specifications for a normalized transpulmonary pressure Ptp_ee_ideal. If it turns out in this examination that this is not the case and that therefore a new (higher or lower) value for the PEEP and/or maximum airway pressure should be adjusted, an occlusion maneuver is carried out in the subsequent breathing cycle at the end of the expiration phase, and the new value for the PEEP is determined on the basis of this occlusion as described hereinbefore. Alternatively, it would also be possible to repeat the occlusion maneuver, as described, every n breathing cycles, with n>1, for example, n=10, 50, or 100.

Figure 3:
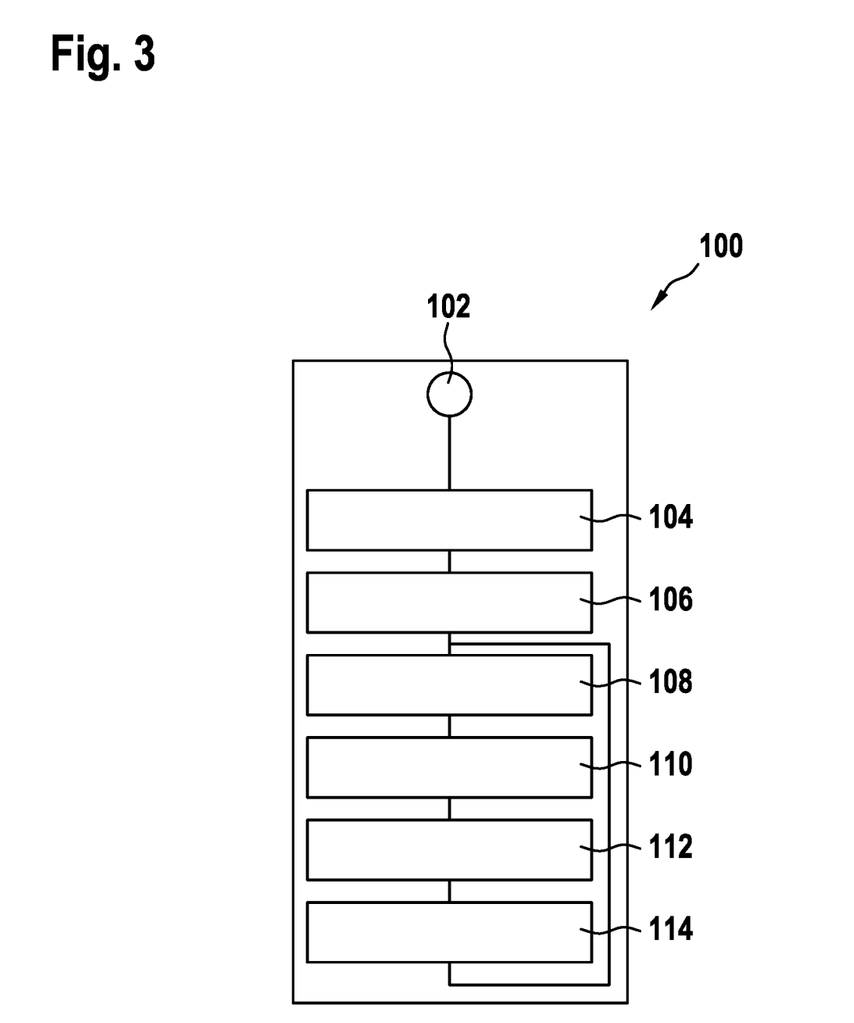
FIG. 3 shows a flowchart for the determination of the PEEP during a breathing cycle with machine ventilation.

FIG. 3 illustrates a flowchart for determining the PEEP and the maximum airway pressure during machine ventilation. This flowchart proceeds continuously during ventilation.

Figure 4A:
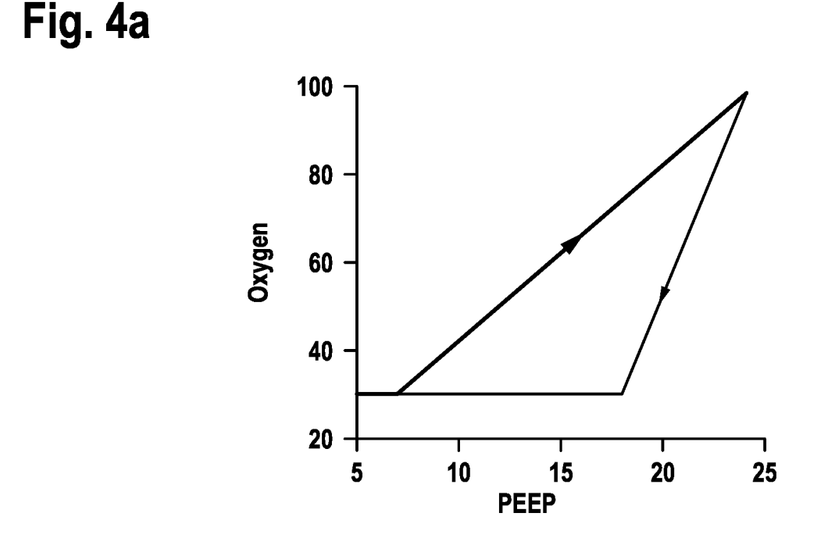
FIGS. 4a and 4b show diagrams illustrating a relationship between oxygen content of the breathing gas FiO2 and PEEP.
Figure 4B:
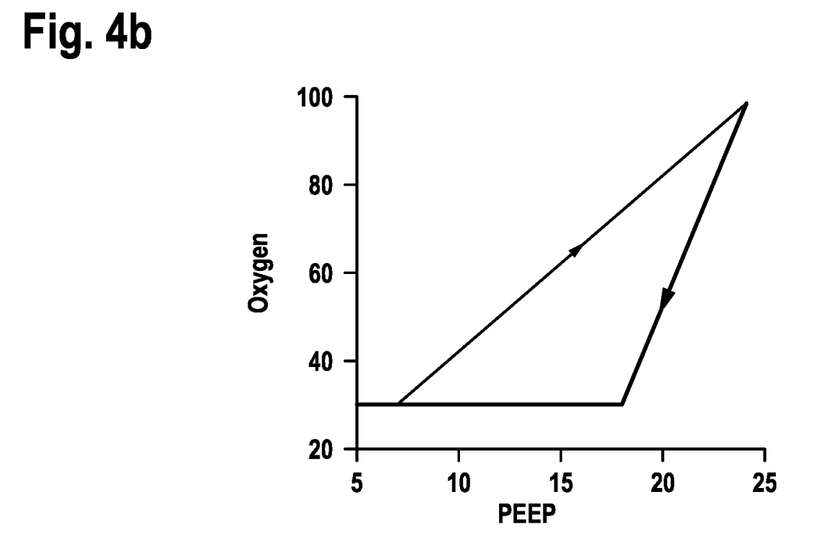

The procedure 100 in FIG. 3 starts in step 102. In the following step 104, a specified or set PEEP is determined. This determination will be based on the percentage of oxygen in the breathing gas FiO2 selected for the patient according to diagnosis or therapy. Such relationships between oxygen content in the breathing gas FiO2 and PEEP were ascertained and published in previous studies, for example, in the above-mentioned ARDSnet Guidelines, The Acute Respiratory Distress Syndrome Network, The New England Journal of Medicine, 2000, 342: pp. 1301-1308 or Grasso et al., American Journal of Respiratory and Critical Care 2007, 176: pp. 761-767. There is often employed a different relationship between the set FiO2 and the PEEP to be adjusted, depending on whether the FiO2 value has been increased since the last set FiO2 value ("increasing therapy") or reduced ("decreasing therapy"). In case of an increasing therapy, there is usually a smaller PEEP adjusted for a given FiO2 value than in case of a decreasing therapy. This is shown e.g., in FIGS. 4a and 4b, with FIG. 4a illustrating the relationship between the oxygen content in the breathing gas FiO2 and the PEEP for increasing therapy, and FIG. 4b illustrating this relationship for decreasing therapy. In each of FIGS. 4a and 4, the line shown as bold line is decisive, as indicated by the arrow. The thin line serves merely for comparison with the respective other line.

In step 106, a (provisional) setting of a maximum airway pressure PInsp_max during the inspiration phase is effected. The maximum airway pressure during the inspiration phase PInsp_max is usually also the largest ever applied airway pressure Paw_max. This pressure is set such that certain critical values with regard to excess stretching of the lungs are not exceeded. A frequently chosen value is Paw_max=30 cm $H_2O$.

Figure 5:
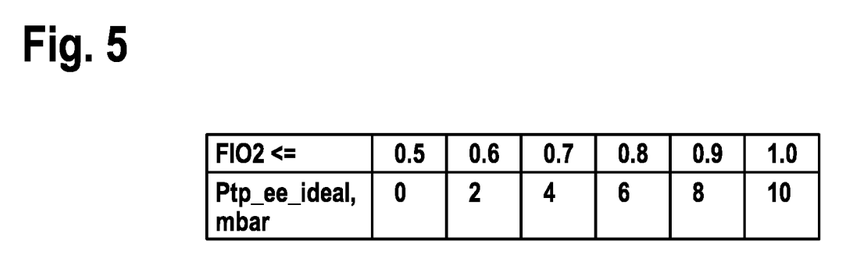
FIG. 5 shows a table indicating a relationship between a normalized transpulmonary pressure at the end of an expiration phase and the oxygen content of the breathing gas FiO2.

In step 108, the airway pressure at the end of the expiration phase Paw_ee and the esophageal pressure at the end of the expiration phase Peso_ee are detected. This can be done e.g., in accordance with the method described hereinbefore, using the airway resistance R, or during an end-expiratory occlusion as described above with reference to FIG. 2. On the basis of the values measured for Paw_ee n and Peso_ee n, a new value is then determined for the PEEP in the subsequent breathing cycle. For determining the new PEEP, one can proceed as follows: from previous studies there is known a relationship between the oxygen content in the breathing gas FiO2 pre-selected for a patient and a normalized (or ideal) transpulmonary pressure at the end of an expiration phase Ptp_ee_ideal. This relationship might look as shown in FIG. 5. An actual transpulmonary pressure at the end of the expiration phase Ptp_ee_n is then determined from the values of Paw_ee n and Peso_ee n determined at the end of an expiration phase. The new PEEP to be adjusted in the subsequent breathing cycle is then determined on the basis of a deviation of the actual transpulmonary pressure Ptp_ee from the transpulmonary pressure associated with the respective FiO2 at the end of an expiration phase Ptp_ee_ideal, in accordance with the formula:

$$PEEP\_n+1 = PEEP\_n + f*(Ptp\_ee\_ideal - Ptp\_ee\_n).$$

In this formula f designates a suitable attenuation factor which usually is chosen between 0 and 1, in particular between 0.1 and 0.8, and preferably between 0.05 and 0.5. In the example described f=0.2.

For suppressing fluctuations, it is also possible to use, instead of the values of Ptp_ee_n and PEEP_n, respectively, measured in the current breathing cycle, a mean value of values determined in m preceding breathing cycles, with m>1.

In step 110, one waits a predetermined number z of breathing cycles, with z≥1. Alternatively, it is also possible to wait a predetermined period of time, and to continue the procedure with the breathing cycle beginning upon expiration of this period of time.

In step 112, the airway pressure at the end of an inspiration phase Paw_ei and the esophageal pressure at the end of an inspiration phase Peso_ei are detected. Peso_ei is detected as described above using the balloon probe 34. Paw_ei can be determined according to the method described with the aid of the airway flows at the end of the inspiration phase V_ei and the airway resistance R. Alternatively, the determination of Paw_ei can be carried out during an occlusion taking place at the end of the inspiration phase, as described above with respect to FIG. 2. Using the measured values of Paw_n_ei and Peso_ei_n, a new value for the maximum pressure is determined then at the end of the inspiration phase Paw_max_n+1. The determination can be carried out according to the following relationship:

$$Paw\_max\_n+1 = [(Paw\_ei\_n - PEEP\_n)/(Ptp\_ei\_n - Ptp\_ee\_n)]$$

* Ptp_ei_max with:

Ptp_ei_max: predetermined maximum transpulmonary pressure at the end
of an inspiration phase, Ptp_ei_n: transpulmonary pressure at the end of an inspiration phase
determined in the current breathing cycle
or in m preceding breathing cycles, Paw_ei_n: airway pressure at the end of an inspiration phase
determined in the current breathing cycle
or in m preceding breathing cycles, PEEP_n: PEEP determined in the current breathing cycle
or in m preceding breathing cycles;
with m≥1.

Step 114 again determines a predetermined number y of breathing cycles waiting time, with y≥1, or alternatively, a predetermined waiting period, after which the process jumps back to the determination of a new PEEP in step 108.

The above-described procedure determines both the positive end-expiratory pressure PEEP and the maximum airway pressure each in patient-related and situation-related manner by way of the respective, currently determined values for the transpulmonary pressure at the end of the expiration phase Ptp_ee and for the transpulmonary pressure at the end of the inspiration phase Ptp_ei. It should be noted that in simpler embodiments, there are also conceivable corresponding procedures in which only a patient-related and situation-related determination of the PEEP is carried out using the transpulmonary pressure at the end of the expiration phase Ptp_ee (and the maximum airway pressure is not determined at all or in a different manner) or in which only a patient-related and situation-related determination of the maximum airway pressure using the transpulmonary pressure at the end of the inspiration phase Ptp_ei is carried out (and the PEEP is not set at all or is set in different manner). The corresponding steps of the above process are then omitted.

The various embodiments described above can be combined to provide further embodiments. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A system, comprising:
 a pressure detection arrangement for detecting a transpulmonary pressure at an end of an expiration phase and/or a transpulmonary pressure at an end of an inspiration phase, and
 a ventilation device for setting a positive end-expiratory pressure based on the transpulmonary pressure detected at the end of the expiration phase,
 wherein the pressure detection arrangement comprises a sensor for determining an alveolar pressure and for determining an esophageal pressure, and determines the respective transpulmonary pressure based on a basis of a difference between the respective alveolar pressure and the respective esophageal pressure,
 wherein the system is designed to determine the positive end-expiratory pressure in a subsequent breathing cycle in accordance with a deviation of the transpulmonary pressure at the end of an expiration phase detected in m preceding breathing cycles from a normalized transpulmonary pressure at the end of an expiration phase, with m≥1.

2. The system of claim 1, wherein the system adjusts the positive end-expiratory pressure set by the ventilation device based on the transpulmonary pressure detected at the end of the expiration phase.

3. The system of claim 1, wherein the system adjusts a maximum airway pressure set by the ventilation device based on the transpulmonary pressure detected at the end of the inspiration phase.

4. The system of claim 3, wherein the system considers the transpulmonary pressure at the end of the expiration phase and the positive end-expiratory pressure when adjusting the maximum airway pressure set by the ventilation device.

5. The system of claim 1, wherein the sensor for determining the esophageal pressure comprises a catheter with balloon probe that is adapted to be inserted into the esophagus for detecting the esophageal pressure.

6. The system of claim 1, wherein the sensor for determining the alveolar pressure is formed such that the sensor determines airway resistance and gas flow in an airway at the end of an expiration phase and/or the gas flow in the airway at the end of an inspiration phase and determines the respective alveolar pressure by way of the respective gas flow and the airway resistance.

7. The system of claim 1, wherein the sensor for determining the alveolar pressure comprises an airway pressure sensor for determining the inlet-side airway pressure and is configured to be arranged at a tube beginning or associated with an airway inlet valve of the ventilation device.

8. The system of claim 7, wherein the sensor for determining the alveolar pressure comprises an arrangement for producing a short-time occlusion of the airway and is configured such that the sensor determines the alveolar pressure at the end of an expiration phase and/or the alveolar pressure at end of an inspiration phase by way of the inlet-side airway pressure detected during an occlusion effected at the end of the expiration phase and/or at the end of the inspiration phase.

9. The system of claim 8, wherein the arrangement for producing a short-time occlusion is designed to cause simultaneous closure of an airway inlet valve and an airway outlet valve of the ventilation device over a predetermined occlusion period.

10. The system of claim 1, wherein the system is designed to determine, based on values determined for a respective breathing cycle, the positive end-expiratory pressure for a subsequent breathing cycle and/or the maximum airway pressure for the subsequent breathing cycle.

11. The system of claim 10, wherein the system is designed to determine the positive end-expiratory pressure for the subsequent breathing cycle and/or the maximum airway pressure for the subsequent breathing cycle by way of m preceding breathing cycles, with m≥1.

12. The system of claim 10, wherein the system is designed to determine, for a respective breathing cycle, a preliminary value for the positive end-expiratory airway pressure in the subsequent breathing cycle and/or a preliminary value for the maximum airway pressure in the subsequent breathing cycle on the basis of the gas flow in the airway at the end of the expiration phase and/or at the end of the inspiration phase and on the basis of the airway resistance and, if the preliminary value for the positive end-expiratory pressure in the subsequent breathing cycle differs from the value set for the positive end-expiratory pressure by a predetermined threshold value or more and/or the preliminary value for the maximum airway pressure in the subsequent breathing cycle differs from the value set for the maximum airway pressure by a predetermined threshold value or more, to determine a new value for the positive end-expiratory pressure in the subsequent breathing cycle and/or a new value for the maximum airway pressure in the subsequent breathing cycle in accordance with a short-time occlusion.

13. The system of claim 10, wherein a starting value for the positive end-expiratory pressure is determined based on a predetermined relationship between the positive end-expiratory pressure and the oxygen content of a breathing gas, the predetermined relationship being dependent on whether the oxygen content of the breathing gas is increased or decreased in relation to the oxygen content set before.

14. The system of claim , wherein the determination of the positive end-expiratory pressure in the subsequent breathing cycle is effected according to the following formula:

$$\text{PEEP}\_n+1 = \text{PEEP}\_n + f^*(Ptp\_ee\_\text{norm} - Ptp\_ee\_n)$$

with:
PEEP_n: positive end-expiratory pressure
in the current breathing cycle
or in m preceding breathing cycles,
Ptp_ee_ideal: normalized transpulmonary pressure
at the end of an expiration phase,
Pt_pee_n: transpulmonary pressure at the end of an expiration phase determined in the current breathing cycle
or in m preceding breathing cycles,
with m≥1, $0 \leq f \leq 1$.

15. The system of claim 14, wherein the normalized transpulmonary pressure at the end of an expiration phase is determined based on a predetermined relationship between the normalized transpulmonary pressure at the end of an expiration phase and the oxygen content of the breathing gas.

16. A system, comprising:
a pressure detection arrangement for detecting a transpulmonary pressure at an end of an expiration phase and/or a transpulmonary pressure at an end of an inspiration phase, and
a ventilation device for setting a pressure based on the transpulmonary pressure detected at the end of the expiration phase and/or the transpulmonary pressure detected at the end of the inspiration phase,
wherein the pressure detection arrangement comprises a sensor for determining an alveolar pressure and for determining an esophageal pressure, and determines the respective transpulmonary pressure based on a basis of a difference between the respective alveolar pressure and the respective esophageal pressure,
wherein the system is designed to compare a positive end-expiratory pressure determined for the subsequent breathing cycle with the positive end-expiratory pressure set for the current breathing cycle, and to change the positive end-expiratory pressure only if the difference between the two values exceeds a predetermined threshold value, and/or to compare a maximum airway pressure determined for the subsequent breathing cycle with the maximum airway pressure set for the current breathing cycle, and to change the maximum airway pressure only when the difference between the two values exceeds a predetermined threshold value.

17. A system, comprising:
a pressure detection arrangement for detecting a transpulmonary pressure at an end of an expiration phase and/or a transpulmonary pressure at an end of an inspiration phase, and a ventilation device for setting a maximum airway pressure based on the transpulmonary pressure detected at the end of the inspiration phase, wherein the pressure detection arrangement comprises a sensor for determining an alveolar pressure and for determining an esophageal pressure, and determines the respective transpulmonary pressure based on a basis of a difference between the respective alveolar pressure and the respective esophageal pressure, wherein the system is designed to determine a maximum airway pressure in the subsequent breathing cycle based on a difference between an airway pressure at the end of an inspiration phase determined in m preceding breathing cycles and a positive end-expiratory pressure applied, applied in m preceding cycles, with m≥1.

18. The system of claim 17, wherein the system is designed to determine the maximum airway pressure in the subsequent breathing cycle according to the following formula:

$$Paw\_max\_n+1 = [(Paw\_ei\_n - PEEP\_n)/(Ptp\_ei\_n - Ptp\_ee\_n)] * Ptp\_ei\_max$$

with:

Ptp_ei_max: predetermined maximum transpulmonary pressure at the end of an inspiration phase, Ptp_ei_n: transpulmonary pressure at the end of an inspiration phase
  determined in the current breathing cycle
  or in m preceding breathing cycles, Ptp_ee_n: transpulmonary pressure at the end of an expiration phase
  determined in the current breathing cycle
  or in m preceding breathing cycles, Paw_ei_n: airway pressure at the end of an inspiration phase
  determined in the current breathing cycle
  or in m preceding breathing cycles, PEEP_n: PEEP determined in the current breathing cycle
  or in m preceding breathing cycles,
  with m≥1.

19. The system of claim 18, wherein the predetermined maximum transpulmonary pressure at the end of an inspiration phase is between 15 and 20 cm $H_2O$.

20. The system of claim 17, wherein a starting value for the maximum airway pressure at the end of an inspiration phase is about 30 cm $H_2O$.

* * * * *

UNITED STATES PATENT AND TRADEMARK OFFICE
CERTIFICATE OF CORRECTION

PATENT NO.         : 11,666,716 B2                                   Page 1 of 1
APPLICATION NO.    : 16/554471
DATED              : June 6, 2023
INVENTOR(S)        : Dominik Novotni et al.

It is certified that error appears in the above-identified patent and that said Letters Patent is hereby corrected as shown below:

In the Claims

Column 16, Claim 14, Line 11:
"The system of claim , wherein" should read: --The system of claim 1, wherein--.

Column 16, Claim 14, Line 15:
"(Ptp_ee_norm - Ptp_ee_n)" should read: --(Ptp_ee_ideal - Ptp_ee_n)--.

Column 16, Claim 14, Line 22:
"Ptp_pee_n:" should read: --Ptp_ee_n:--.

Column 17, Claim 18, Line 18:
"[(Paw_ei_n - PEEP_n)/(Ptp_ee_n -)]" should read: --[(Paw_ei_n - PEEP_n)/(Ptp_ei_n - Ptp)]--.

Signed and Sealed this
Fifteenth Day of July, 2025

Coke Morgan Stewart
*Acting Director of the United States Patent and Trademark Office*